United States Patent [19]

Eyer et al.

[11] Patent Number: 5,434,269
[45] Date of Patent: Jul. 18, 1995

[54] ASYMMETRIC HYDROGENATION OF FUROIMIDAZOLE DERIVATIVES

[75] Inventors: Martin Eyer, Brig-Glis, Switzerland; Ronald E. Merrill, Torrance, Calif.

[73] Assignee: Lonza Ltd., Gampel/Valais, Switzerland

[21] Appl. No.: 285,759

[22] Filed: Aug. 3, 1994

Related U.S. Application Data

[63] Continuation of Ser. No. 49,295, Apr. 20, 1993, abandoned.

[51] Int. Cl.⁶ .............. C07D 491/048; C07D 491/044
[52] U.S. Cl. .................. 548/303.1; 548/302.7; 548/301.7; 548/300.1
[58] Field of Search ...................... 548/303.1

[56] References Cited

U.S. PATENT DOCUMENTS

| | | | |
|---|---|---|---|
| 4,409,392 | 10/1983 | Paxson | 562/496 |
| 5,162,540 | 11/1992 | McGarrity et al. | 548/303.1 |
| 5,171,892 | 12/1992 | Burk | 568/12 |
| 5,187,136 | 2/1993 | Klobucas et al. | 502/162 |

FOREIGN PATENT DOCUMENTS

| | | |
|---|---|---|
| 0270076 | 6/1988 | European Pat. Off. |
| 0273270 | 7/1988 | European Pat. Off. |
| 2058248 | 6/1971 | Germany |

OTHER PUBLICATIONS

T. Hayashi et al., Bull. Chem. Soc. Japan, 53, (1980), pp. 1138–1151.
Chatt et al., J. Chem. Soc., (1957), pp. 4735–4741.
Giordano et al., Inorg. Synth., 19, (1979), pp. 218 to 220.
Noyori et al, Acc. Chem. Res 1990, 23, pp.345 to 350 (Oct. 1990).

*Primary Examiner*—Mary C. Lee
*Assistant Examiner*—Laura L. Stockton
*Attorney, Agent, or Firm*—Fisher, Christen & Sabol

[57] ABSTRACT

A process for the asymmetric hydrogenation of furoimidazole derivatives of the general formula:

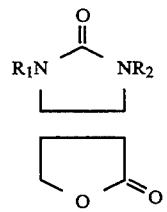

I with hydrogen in the presence of a homogeneous catalyst to give the corresponding diastereomeric dihydrofuroimidazole derivatives of the general formula:

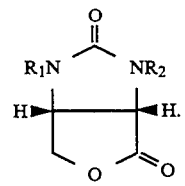

II $R_1$ and $R_2$ are protective groups, although $R_2$ can be hydrogen. The dihydrofuroimidazole derivatives of the general formula II are intermediates for the preparation of (+)-biotin.

12 Claims, No Drawings

ASYMMETRIC HYDROGENATION OF FUROIMIDAZOLE DERIVATIVES

This application is a Continuation of prior U.S. application Ser. No. 08/049,295 filed Apr. 20, 1993 now abandoned.

BACKGROUND OF THE INVENTION

1. Field Of The Invention

The invention relates to a novel process for the asymmetric hydrogenation of furoimidazole derivatives of the general formula:

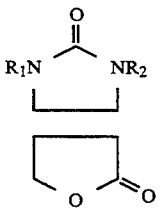
I wherein $R_1$ denotes a protective group which can be removed by methods known in the art and $R_2$ represents hydrogen or a protective group which can be removed by methods known in the art, in the presence of a homogeneous catalyst with hydrogen to give the corresponding diastereomeric dihydrofuroimidazole derivatives of the general formula:

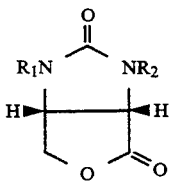
II wherein $R_1$ and $R_2$ have the above-mentioned meaning.

The dihydrofuroimidazoles of the general formula II are important intermediates in the synthesis of (+)-biotin, an essential vitamin for humans which is also termed vitamin H. (+)-Biotin is also used as a pharmaceutical for the treatment of dermatosis or as a feed additive having growth-promoting activity for farm animals.

2. Background Art

The majority of the known (+)-biotin syntheses pursue the aim of separating appropriate precursors via some highly laborious racemate cleavage methods using some highly expensive cleavage agents and using the resulting diastereomers to further pursue the (+)-biotin synthesis (cf., for example German Patent No. 2,058,248). According to European Published Patent Application No. 273,270, the introduction of the relevant optically active center, that is, the 3aS and 6aR positions of the biotin ring structure, was achieved for the first time via an asymmetric hydrogenation of corresponding furoimidazole derivatives using a classical hydrogenation catalyst, such as, rhodium on aluminum oxide. This prior art process was not completely satisfactory with respect to the attainable yield of the desired diastereomers.

BROAD DESCRIPTION OF THE INVENTION

The main object of the invention is to provide an improved asymmetric hydrogenation process by which the above-mentioned key step of the biotin synthesis can be carried out with a very good diastereoselectivity with good yield of the dihydrofuroimidazole. Other objects and advantages of the invention are set out herein or are obvious herefrom to one skilled in the art.

The objects and advantages of the invention are achieved by the process according to the invention.

The furoimidazoles of the general formula I can be prepared according to the directions of European Published Patent Application No. 273,270 or European Published Patent Application No. 270,076.

The invention involves a process for the asymmetric hydrogenation of furoimidazole derivatives of the general formula:
wherein $R_1$ denotes a protective group which can be removed by methods known in the art and $R_2$ denotes hydrogen or a protective group which can be removed by methods known in the art, in the presence of a homogeneous catalyst with hydrogen to give the corresponding diastereomeric dihydrofuroimidazole derivatives of the general formula:

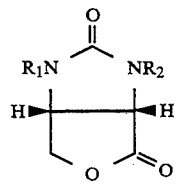
II wherein $R_1$ and $R_2$ have the above-mentioned meaning. Homogeneous catalysts are used which are obtainable by reaction of an Rh complex with a chiral ferrocenylphosphine ligand of the general formula:

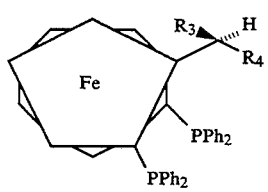
III wherein $R_3$ denotes a $(C_1-C_6)$-alkyl group, $R_4$ denotes a group $—OR_5$ wherein $R_5$ denotes hydrogen or a

$—CR_6$ group wherein $R_6$ denotes a $(C_1-C_6)$-alkyl group which is unsubstituted or substituted by an acetyl group, a carbamoyl group or a halogen atom, or $R_4$ denotes a $—NR_7R_8$ group wherein $R_7$ denotes hydrogen, a $(C_1-C_6)$-alkyl group or a hydroxyethyl group and $R_8$ denotes an N,N-dimethylaminoethyl-, a hydroxyethyl-, an (S)-prolinoyl-, a morpholinoethyl- or an N-methyl-piperazinylethyl group and Ph denotes a phenyl group.

Preferably the groups which can be removed by methods known in the art used for $R_1$ are phenyl-$(C_1-C_6)$-alkyl groups, benzyl groups or naphthyl-$(C_1-C_6)$-alkyl groups, the aromatic nuclei of each of the groups being unsubstituted or substituted by one or more substituents selected from the group comprising ($C_1-C_6$)-alkyl, ($C_1-C_6$)-alkoxy, hydroxy, halogen, amino, ($C_1-C_6$)-alkylamino and ($C_1-C_6$)-dialkylamino. Preferably the groups which can be removed by methods known in the art represented by $R_2$ are ($C_1-C_6$)-alkanoyl groups, ($C_1-C_6$)-alkoxy-($C_1-C_6$)-alkyl groups, ($C_1-C_6$)-alkoxycarbonyl groups, or aroyl or benzyl groups which are unsubstituted or substituted by one or more substituents selected from the group comprising ($C_1-C_6$)-alkyl, ($C_1-C_6$)-alkoxy, hydroxy, halogen, amino, ($C_1-C_6$)-alkylamino and ($C_1-C_6$)-dialkylamino. Preferably the chiral ferrocenylphosphine ligand used is the (R)(S)-BPPFOAc/general formula III where $R_3$ is $CH_3$, $$R_4 \text{ is } -O-\overset{O}{\underset{\|}{C}}-CH_3$$

or (R)(S)-BPPFA/general formula III where $R_3$ is $CH_3$, $R_4$ is $-N(CH_3)_2$ or (R)(S)-BPPFOH/general formula III where $R_3$ is $CH_3$, $R_4$ is $-OH$.

Preferably Rh complexes of the general formula:

$$Rh(O): [Rh(L)A]_2 \qquad \qquad IV$$

or $$Rh(+): [Rh(L)_2]B^- \qquad \qquad V,$$

are used, wherein L denotes two $C_2-C_{12}$ olefins or a $C_5-C_{12}$ diene and A signifies a halogen and $B^-$ signifies an anion from an oxo acid or a complex acid.

Preferably the reaction proceeds at a hydrogen pressure of 1 to 200 bar and a reaction temperature of 25° to 150° C. Preferably the amount of catalyst expressed as a ratio of furoimidazole to homogeneous catalyst varies in the range 100:1 and 5000:1. Preferably aprotic solvents are used. Preferably the aprotic solvent is toluene.

DETAILED DESCRIPTION OF THE INVENTION

The protective groups which can be removed by methods known in the art expediently used for $R_1$ are the following groups: A phenyl-($C_1-C_6$)-alkyl group, a benzyl group or a naphthyl-($C_1-C_6$)-alkyl group. Aromatic nuclei thereof can be unsubstituted or substituted by one or more substituents selected from the group comprising ($C_1-C_6$)-alkyl, ($C_1-C_6$)-alkoxy, hydroxy, halogen, amino, ($C_1-C_6$)-alkylamino and ($C_1-C_6$)-dialkylamino. The phenyl-($C_1-C_6$)-alkyl group or the naphthyl-($C_1-C_6$)-alkyl group can contain a chiral center in the alkyl moiety.

$R_1$ preferably is a (R) or (S)-1-phenylethyl group, a benzyl group or a (R) or (S)-1-naphthylethyl group. The aromatic nuclei of these preferred groups can be unsubstituted or substituted with the above-mentioned substituents.

$R_2$ can be hydrogen or protective groups which can be removed by methods known in the art selected from the group comprising, ($C_1-C_6$)-alkanoyl, benzyl, ($C_1-C_6$)-alkoxy-($C_1-C_6$)-alkyl, ($C_1-C_6$)-alkoxycarbonyl and aroyl, such as, benzoyl. $R_2$ preferably is hydrogen, acetyl, benzyl, ($C_1-C_2$)-alkoxy-($C_1-C_2$)-alkyl, ($C_1-C_2$)-alkoxycarbonyl or benzoyl. The aromatic nucleus of the benzyl group or of the aroyl groups can be substituted in accordance with the aromatic nuclei of $R_1$.

Surprisingly it has been found that homogeneous catalyst which are obtainable by reaction of a Rh complex with a chiral ferrocenylphosphine ligand of the general formula:

III wherein $R_3$ denotes a ($C_1-C_6$)-alkyl group, $R_4$ denotes a group $-OR_5$ wherein $R_5$ denotes hydrogen or a $$-\overset{O}{\underset{\|}{C}}R_6$$

group wherein $R_6$ denotes a ($C_1-C_6$)-alkyl group which is unsubstituted or substituted by an acetyl group, a carbamoyl group or a halogen atom, or $R_4$ denotes a $-NR_7R_8$ group wherein $R_7$ denotes hydrogen, a ($C_1-C_6$)-alkyl group or a hydroxyethyl group and $R_8$ denotes an N,N-dimethylaminoethyl-, a hydroxyethyl-, an (S)-prolinoyl-, a morpholinoethyl- or an N-methyl-piperazinylethyl group and Ph denotes a phenyl group, or $R_4$ denotes $-N(CH_3)_2$ show, in comparison to the process of the prior art, a highly increased diastereoselectivity with simultaneously good yield.

Preferred chiral ferrocenylphosphine ligands written in the abbreviated form conventional for those skilled in the art are:

(R)(S)-BPPFOAc/general formula III where $R_3$ is $CH_3$, $$R_4 \text{ is } -O-\overset{O}{\underset{\|}{C}}-CH_3$$

or (R)(S)-BPPFA/general formula III where $R_3$ is $CH_3$, $R_4$ is $-N(CH_3)_2$ or (R)(S)-BPPFOH/general formula III where $R_3$ is $CH_3$, $R_4$ is $-OH$.

The above-mentioned ferrocenylphosphine ligands are disclosed in the literature (see, for example, T. Hayashi et al., Bull. Chem. Soc. Japan, (1980), 53, 1138–1151]. The Rh complexes used are those of the general formula:

$$Rh(O): [Rh(L)A]_2 \qquad \qquad IV$$

or $$Rh(+): [Rh(L)_2]B^- \quad V,$$

wherein L denotes two $C_2$-$C_{12}$ olefins or a $C_5$-$C_{12}$ diene, A denotes a halogen and $B^-$ denotes an anion from an oxo acid or a complex acid. L preferably is two $C_2$-$C_6$ olefins or a $C_5$-$C_8$ diene. The diene can be acyclic, mono- or bicyclic. Examples of olefins are ethylene, propene and 1-butene. Examples of dienes are 1,5-hexadiene, 1,4-cyclohexadiene, 1,4- and 1,5-heptadiene, 1,4- and 1,5-cycloheptadiene, 1,4- and 1,5-octadiene, 1,4- and 1,5-cyclooctadiene, and norbornadiene. The most preferable meaning of L is two ethylene, 1,5-hexadiene, 1,5-cyclooctadiene or norbornadiene. A preferably A denotes chlorine or bromine. Examples of $B^-$ are $ClO_4^-$, $FSO_3^-$, $CH_3SO_3^-$, $CF_3SO_3^-$, $BF_4^-$, $PF_6^-$, $SbCl_6^-$, $AsF_6^-$ and $SbF_6^-$. Preferred anions $B^-$ are $BF_4^-$, $ClO_4^-$, $PF_6^-$, $CF_3SO_3^-$ and $SbF_6^-$.

The preparation of these Rh complexes is known and follows, for example, from J. Chatt et al., J. Chem. Soc., (1957), 4735–4741, or G. Giordano et al., Inorg. Synth., (1979), 19, 218.

The preparation of the active homogeneous catalyst is expediently carried out in situ, that is, in the context of the hydrogenation of the relevant furoimidazole of the general formula I. The procedure is expediently carried out in such a manner that the homogeneous catalyst components, that is, the Rh complex and the corresponding phosphine ligand, together with the corresponding furoimidazole derivative are first placed in a suitable inert solvent. By means of appropriate precautions, care should be taken that the reaction is preferably carried out in an oxygen-free inert gas atmosphere.

It was found that the solvents best suited for the hydrogenation are aprotic and can be applied either separately or as a mixture. Expediently used are aliphatic, aromatic or halogenated hydrocarbons. Representatives of aliphatic hydrocarbons are pentane and hexane. Representatives of aromatic hydrocarbons are benzene, toluene and xylene. Representatives of halogenated hydrocarbons are methylene chloride and chloroform. The most preferably solvent is toluene. It can be advantageous to add a protic solvent like an aliphatic alcohol. Preferably methanol is used as the aliphatic alcohol. The amount of solvent is expediently selected so that a substrate concentration of 2 to 20 percent is obtained. A substrate concentration of 10 percent is preferably employed.

The amount of catalyst expressed as a ratio of substrate (furoimidazole) to catalyst expediently varies between 100:1 and 5000:1, preferably in the range of about 500:1. The reaction advantageously proceeds at a hydrogen pressure between 1 bar and 200 bar, preferably 1 bar to 20 bar, and at a reaction temperature between 25° and 150° C., preferably 40° and 90° C.

Thereafter the desired diastereomeric (3aS-6aR)-dihydrofuroimidazole of the general formula II can be isolated in a manner conventional to those skilled in the art. By recrystallization using an appropriate aprotic solvents, such as, methyl isobutyl ketone, ethyl acetate and toluene, any portions of the undesired (3aR-6aS)-dihydrofuroimidazole can be eliminated.

The resulting dihydrofuroimidazoles can then be further converted to the (+)-biotin, for example, in accordance with European Published Patent Application No. 273,270.

EXAMPLE 1

A high-pressure stainless steel autoclave was charged with 3.00 g of 1-benzyl-1H-furo[3,4-d]imidazole-2,4-(3H,6H)-dione, 13.7 mg of chlororhodium (1,5-cyclooctadiene) dimer and 35.9 mg of (R)(S)-BPPFOAc. The vessel was flushed with argon and 150 ml of oxygen-free dichloromethane was added. The system was pressurized to 14 bar with hydrogen and the reaction was conducted at 45° for 24 hours. HPLC analysis showed 93 percent conversion. The pressure was released, and the solution was treated with Dowex 50X2-400 to remove the catalyst and evaporated. 2.85 g of product were obtained, with rotation −35.3 (1, acetone), corresponding to 52 percent ee (enantiomeric excess).

EXAMPLE 2

A high-pressure stainless steel autoclave was charged with 3.40 g of 1-[(R)-1-phenylethyl]-1H-furo[3,4-d]imidazole-2,4-(3H,6H)-dione, 13.7 mg of chlororhodium (1,5-cyclooctadiene)-dimer and 35.1 mg of (R)(S)-BPPFA. The vessel was flushed with argon and 75 ml of oxygen-free toluene was added. The system was pressurized to 4.2 bar with hydrogen and the reaction was conducted at 90° C. for 20 hours. HPLC analysis showed 98 percent conversion and 38 percent de (diastereomeric excess) favoring the desired RRS isomer.

EXAMPLE 3

A high-pressure stainless steel autoclave was charged with 3.40 g of 1-[(R)-1-phenylethyl]-1H-furo[3,4-d]imidazole-2,4-(3H,6H)-dione, 13.7 of chlororhodium (1,5-cyclooctadiene)-dimer and 35.9 mg of (R)(S)-BPPFOAc. The vessel was flushed with argon and 75 ml of oxygen-free toluene was added. The system was pressurized to 5.6 bar with hydrogen and the reaction was conducted at 90° C. for 4 hours. HPLC analysis showed 98 percent conversion and 58 percent de (diastereomeric excess) favoring the desired RRS isomer.

EXAMPLE 4

A high-pressure stainless steel autoclave was charged with 244.3 g of 1-[(R)-1-phenylethyl]-1H-furo[3,4-d]imidazole-2,4-(3H,6H)-dione, 490 mg of chlororhodium (1,5-cyclooctadiene)-dimer and 1.28 g of (R)(S)-PPPFOAc. The vessel was flushed with argon and 2500 ml of oxygen-free toluene was added. The system was pressurized to 14 bar with hydrogen and the reaction was conducted at 90° C. for 2 hours. HPLC analysis showed 99 percent conversion and 69 percent de (diastereomeric excess) favoring the desired RRS isomer. The pressure was released and the vessel was flushed with nitrogen. The reaction mixture was cooled to 0 degrees and filtered. The crude product was recrystallized from methyl isobutyl ketone to give 192 grams of pure product in 78 percent yield.

What is claimed is:

1. A process comprising the asymmetric hydrogenation of a furoimidazole derivative of formula:

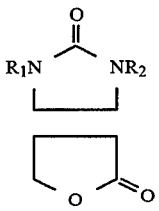

(I)

wherein $R_1$ is a protective group selected from the group consisting of phenyl-$(C_1-C_6)$-alkyl, benzyl and naphthyl-$(C_1-C_6)$-alkyl, the aromatic nuclei of each of the groups being unsubstituted or substituted by one or more substituents selected from the group consisting of $(C_1-C_6)$-alkyl, $(C_1-C_6)$-alkoxy, hydroxy, halogen, amino, $(C_1-C_6)$-alkylamino and $(C_1-C_6)$-dialkylamino, and $R_2$ is hydrogen or a protective group, selected from the group consisting of $(C_1-C_6)$-alkanoyl, $(C_1-C_6)$-alkoxy-$(C_1-C_6)$-alkyl, $(C_1-C_6)$-alkoxycarbonyl, aroyl and benzyl, said aroyl or benzyl being unsubstituted or substituted by one or more substituents selected from the group consisting of $(C_1-C_6)$-alkyl, $(C_1-C_6)$-alkoxy, hydroxy, halogen, amino, $(C_1-C_6)$-alkylamino and $(C_1-C_6)$-dialkylamino, in the presence of a homogeneous catalyst with hydrogen to give a corresponding diastereomeric dihydrofuroimidazole derivative of formula:

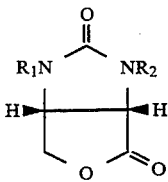

(II)

wherein $R_1$ and $R_2$ have the above-mentioned meanings, the homogeneous catalyst having been obtained by reaction of a Rh complex with a chiral ferrocenylphosphine ligand of formula:

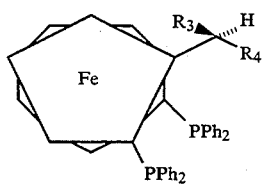

(III)

wherein
$R_3$ is $(C_1-C_6)$-alkyl,
$R_4$ is $-OR_5$ wherein
$R_5$ is hydrogen or

wherein
$R_6$ is $(C_1-C_6)$-alkyl which is unsubstituted or substituted by acetyl, carbamoyl or halogen, or
$R_4$ is $-NR_7R_8$ wherein
$R_7$ is hydrogen, $(C_1-C_6)$-alkyl or hydroxyethyl and $R_8$ is N,N-dimethylaminoethyl-, hydroxyethyl-, (S)-prolinoyl-, morpholinoethyl- or N-methylpiperazinylethyl and
Ph denotes phenyl or $R_4$ is $-N(CH_3)_2$.

2. The process according to claim 1 wherein the chiral ferrocenylphosphine ligand used is the (R)(S)-BPPFOAc/ formula III where $R_3$ is $CH_3$, $$R_4 \text{ is } -O-\overset{\overset{O}{\|}}{C}-CH_3$$

or
(R)(S)-BPPFA/ formula III where $R_3$ is $CH_3$, $R_4$ is $-N(CH_3)_2$ or
(R)(S)-BPPFOH/ formula III where $R_3$ is $CH_3$, $R_4$ is $-OH$.

3. Process according to claim 2 wherein a Rh complex of formula:

Rh(O): $[Rh(L)A]_2$      IV or

Rh(+): $[Rh(L)_2]B^-$      V, is used, wherein L is two $C_2-C_{12}$ olefins or a $C_5-C_{12}$ diene, A is a halogen and $B^-$ is an anion from an oxo acid or a complex acid.

4. The process according to claim 3 wherein the reaction proceeds at a hydrogen pressure of 1 to 200 bar and a reaction temperature of 25° to 150° C.

5. The process according to claim 4 wherein the amount of catalyst expressed as a ratio of furoimidazole to homogeneous catalyst varies in the range 100:1 and 5000:1.

6. The process according to claim 5 wherein an aprotic solvent is used in the hydrogenation.

7. The process according to claim 6 wherein the aprotic solvent is toluene.

8. Process according to claim 1 wherein a Rh complex of the formula:

Rh(O): $[Rh(L)A]_2$      IV or

Rh(+): $[Rh(L)_2]B^-$      V, is used, wherein L is two $C_2-C_{12}$ olefins or a $C_5-C_{12}$ diene, A is a halogen and $B^-$ is an anion from an oxo acid or a complex acid.

9. The process according to claim 1 wherein the reaction proceeds at a hydrogen pressure of 1 to 200 bar and a reaction temperature of 25° to 150° C.

10. The process according to claim 1 wherein the amount of catalyst expressed as a ratio of furoimidazole to homogeneous catalyst varies in the range 100:1 and 5000:1.

11. The process according to claim 1 wherein an aprotic solvent is used in the hydrogenation.

12. The process according to claim 1 wherein the aprotic solvent is toluene.

* * * * *